United States Patent [19] [11] Patent Number: 4,481,204
Szántay et al. [45] Date of Patent: Nov. 6, 1984

[54] E-HOMO-EBURNANE DERIVATIVES, PROCESS FOR THEIR PREPARATION, AND PHARMACEUTICAL COMPOSITIONS CONTAINING THESE COMPOUNDS

[75] Inventors: Csaba Szántay; Lajos Szabó; György Kalaus; János Sápi; Éva Pálosi; Egon Kárpáti; László Szporny, all of Budapest, Hungary

[73] Assignee: Richter Gedeon Vegyészeti Gyár R.T., Budapest, Hungary

[21] Appl. No.: 509,150

[22] Filed: Jun. 29, 1983

[51] Int. Cl.³ ................. A61K 31/395; C07D 471/22; C07D 459/00; C07D 461/00
[52] U.S. Cl. ............................. 424/262; 260/239.3 P; 260/243.3; 260/244.4
[58] Field of Search ...................... 260/239.3 P, 243.3, 260/244.4; 424/262

[56] References Cited
U.S. PATENT DOCUMENTS 4,283,401 8/1981 Szantay et al. .............. 260/239.3 P
4,285,950 8/1981 Szantay et al. .............. 260/239.3 P Primary Examiner—Robert T. Bond
Attorney, Agent, or Firm—Keil & Weinkauf

[57] ABSTRACT

The invention relates to racemic or optically active E-homo-eburnane derivatives of the formula /I/,

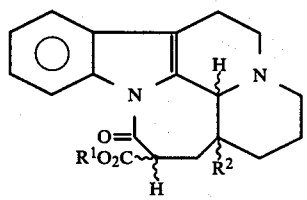

/I/ wherein
$R^1$ and $R^2$ independently represent an alkyl group having 1 to 6 carbon atoms,
and acid addition salts thereof.

The new compounds are pharmaceutically active, for example their certain representatives, in particular from the cis-series, show antidepressive activity, while others, especially the compounds of the trans-series, are potent anthypoxial agents. The compounds of the formula /I/ and pharmaceutically acceptable acid addition salts thereof can therefore be employed as active ingredients of pharmaceutical compositions.

6 Claims, No Drawings

E-HOMO-EBURNANE DERIVATIVES, PROCESS FOR THEIR PREPARATION, AND PHARMACEUTICAL COMPOSITIONS CONTAINING THESE COMPOUNDS

This invention relates to new E-homo-eburnane derivatives, process for their preparation, and pharmaceutical compositions containing them as active ingredient. More particularly, the invention concerns new racemic or optically active E-homo-eburnane derivatives of the formula /I/,

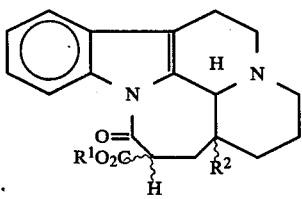

wherein
$R^1$ and $R^2$ independently represent an alkyl group having 1 to 6 carbon atoms,
and acid addition salts thereof.

According to another aspect of the invention there is provided a process for the preparation of racemic or optically active E-homo-eburnane derivatives of the formula /I/, which process comprises subjecting a racemic or optically active octahydroindolo[2,3-a]quinoline derivative of the formula /II/,

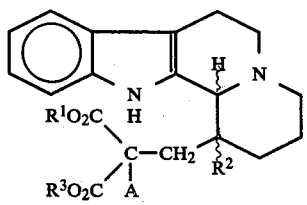

wherein
A is hydrogen or a $-CH_2-CH/CO_2R^1/_2$ or $-CH_2-C/CO_2R^1/_2-CH_2-CH/CO_2R^1/_2$ group, in which
$R^1$ and $R^2$ are as defined above,
$R^3$ is identical with $R^1$ or, if A represents hydrogen, $R^3$ may also stand for hydrogen,
or an acid addition salt thereof to ring closure, resolving, if desired, the compounds of the formula /I/ obtained and/or converting the racemic or optically active compounds of the formula /I/ into acid addition salts thereof.

The compounds of the formula /I/ are pharmaceutically active, for example their certain representatives, in particular those from the cis-series, show antidepressive activity, while others, especially the compounds of the trans-series, are potent antihypoxial agents.

According to a further aspect of the invention there are provided pharmaceutical compositions, which comprise as an active ingredient at least one racemic or optically active E-homo-eburnane derivative of the formula /I/ or a pharmaceutically acceptable acid addition salt thereof, in admixture with inert solid or liquid pharmaceutical carriers and/or additives.

The term "alkyl group having 1 to 6 carbon atoms" as used herein means straight or branched chained aliphatic hydrocarbon groups having 1 to 6 carbon atoms, e.g. methyl, ethyl, n-propyl, isopropyl, n-butyl, sec.-butyl, tert.-butyl, n-pentyl, isopentyl, n-hexyl or isohexyl groups, etc.

If desired, the compounds of the formula /I/ may be converted into their acid addition salts. Suitable acids for this purpose include inorganic acids, such as hydrogen halides, e.g. hydrochloric acid, hydrogen bromide, sulfuric acid, phosphoric acid, nitric acid, perhaloic acids e.g. perchloric acid, etc.; organic carboxylic acids such as formic acid, acetic acid, propionic acid, glycolic acid, maleic acid, hydroxymaleic acid, fumaric acid, succinic acid, tartaric acid, ascorbic acid, citric acid, malic acid, salicylic acid, lactic acid, cinnamic acid, benzoic acid, phenylacetic acid, p-amino-benzoic acid, p-hydroxy-benzoic acid, p-amino-salicylic acid, etc.; alkylsulfonic acids, such as methanesulfonic acid, ethanesulfonic acid, etc.; cycloaliphatic acids, e.g. cyclohexylsulfonic acid; arylsulfonic acids, e.g. p-toluenesulfonic acid, naphthylsulfonic acid, sulfanylic acid, etc.; amino acids, such as asparaginic acid, glutaminic acid, N-acetyl-asparaginic acid, N-acetyl-glutaric acid, etc.

The starting compounds of the formula /II/ can be prepared as described in the Belgian patent specification No. 883,576 by electrophilic alkylation of the corresponding hexahydroindolo[2,3-a]quinolizinium salts with a methylenemalonic acid dialkylester and subsequent hydrogenation and, if desired, a further partial hydrolysis.

The cyclization of the compounds of the formula /II/, in which A stands for a hydrogen atom or a $CH_2-CH/CO_2R^1/_2$ or $-CH_2-C/CO_2R^1/_2-CH_2-CH/CO_2R^1/_2$ group, $R^3$ has the same meaning as $R^1$ and $R^1$ and $R^2$ are as defined above, can be carried out with sufficiently strong bases, e.g. alkali metal hydrides, such as sodium hydride, potassium hydride, etc., alkali metal alcoholates, such as potassium or sodium ethylate, preferably potassium tert.-butylate in aprotic organic solvents, such as xylene, toluene, preferably benzene. The cyclization is preferably performed at the boiling temperature of the reaction mixture. The reaction is completed in a very short time, generally in 10 to 40 minutes, preferably 15 to 30 minutes.

The ring closure of the compounds of the formula /II/, in which A and $R^3$ stand for a hydrogen atom, $R^1$ and $R^2$ have the same meaning as defined above, is carried out with a dehydrating agent, preferably phosphorus oxychloride or phosphorus pentoxide, preferably in an organic solvent inert under the reaction conditions, such as aromatic hydrocarbons, preferably benzene, or chlorinated hydrocarbons, e.g. chloroform or carbon tetrachloride.

If the compounds of the formula /II/ are used in the form of their acid addition salts, e.g. hydrogen halides, perchlorates, etc., it is preferred to set free the basic compounds from their salts before cyclization. The liberation of the bases can for example be carried out with a dilute aqueous solution of an inorganic base, such as an alkali metal carbonate, e.g. sodium carbonate, potassium carbonate, an alkali metal hydroxide, e.g. sodium hydroxide, potassium hydroxide, etc., in a water-immiscible inert organic solvent, such as halogenated hydrocarbons, e.g. dichloromethane, chloroform etc.

By the process according to the invention both cis- and trans-compounds of the formula /I/ can be prepared from the corresponding cis- and trans-compounds of the formula /II/, respectively.

By the process according to the invention racemic and optically active compounds of the formula /I/ can equally be prepared. Starting from racemic compounds, racemic end products of the formula /I/ are obtained which, if desired, can be resolved by conventional techniques. From optically active starting compounds directly optically active end products can be obtained.

The racemic or optically active compounds of the formula /I/ can be converted into their acid addition salts with an organic or inorganic acid.

The salts are generally prepared in an inert organic solvent, for example in an aliphatic alcohol having 1 to 6 carbon atoms, by dissolving the racemic or optically active compounds of the formula /I/ in said solvent, adding the corresponding acid into the solution while the pH becomes slightly acidic /about pH 6/ and subsequently separating the acid addition salt obtained from the reaction mixture preferably by precipitating with a water-immiscible organic solvent, such as diethyl ether.

If desired, the racemic or optically active compounds of the formula /I/ or acid addition salts thereof may be subjected to further purification, e.g. recrystallization. The solvents used for recrystallization are selected in accordance with the solubility and crystallizability of the compounds to be recrystallized.

The antihypoxial activity of certain compounds within the scope of the invention, particularly of $3\beta,17\alpha$-trans-derivatives was tested on the survival time of mice, in normobaric hypoxia.

The test was carried out as follows:

Five male mice are placed into a 3-liter glass cylinder through which a mixture of 96% nitrogen and 4% oxygen is passed. The interval between placing the mice into the cylinder and the death of the animals is measured. Animals living at least twice as long as the average survival time of the untreated animals are considered protected. The animals are treated in groups of 10, administering an intraperitoneal dose of 50 mg./kg. of bodyweight 30 minutes before placing them into the glass cylinder.

The results are set forth in the following Table.

TABLE

| Compound | Survival time Average min. | % | Protection % |
|---|---|---|---|
| /±/-Trans-14-oxo-15-ethoxy-carbonyl-E—homo-eburnane /3β,17α/ | 8.3 ± 1.1 | +32 | 20 |
| Control | 6.3 ± 1.45 | — | 0 |
| Vincamine | 7.1 ± 1.30 | +13 | 0 |

Of the compounds of the formula /I/ especially the $3\beta,17\alpha$-cis compounds are potent antidepressive agents.

The active ingredients of the formula /I/ or pharmaceutically acceptable acid addition salts thereof can be converted into pharmaceutical compositions for parenteral or enteral administration by admixing them with solid and/or liquid carriers and/or further additives conventionally used in the preparation of pharmaceutical compositions. As a carrier for example water, gelatine, lactose, starch, pectine, magnesium stearate, stearic acid, talc, vegetable oils, e.g. peanut oil, olive oil, etc. can be employed.

The compositions may be finished in the form of solid, e.g. tablets, lozenges, dragées, capsules, such as hard gelatine capsules, suppositories, etc. or liquid, e.g. oily or aqueous solutions, suspensions, emulsions, syrups, soft gelatine capsules, injectable oily or aqueous solutions or suspensions, etc. formulations. The quantity of the solid carrier can be varied within a wide range but preferably is between about 25 mg. and 1 g. The pharmaceutical compositions optionally contain also conventional pharmaceutical additives, such as preservatives, stabilizing, wetting, emulsifying agents, salts capable of adjusting the osmotic pressure, buffers, flavouring agents, aroma agents, etc. Optionally further pharmaceutically active compounds can also be present in the formulations.

The pharmaceutical compositions are preferably manufactured in dosage units, suitable for the desired route of administration. The pharmaceutical compositions may be prepared by conventional techniques, which comprise for example screening, admixing, granulating, pressing or dissolving of the components. The compositions obtained can be subjected to further operations conventionally used in the pharmaceutical industry, for example sterilization.

Further details of the present invention are to be found in the following Examples which are, however, by no means intended to limit the scope of the protection sought.

EXAMPLE 1

/±/-Cis-14-oxo-15-ethoxycarbonyl-E-homo-eburnane/3α,17α/

From 800 mg. /1.90 mmoles/ of /±/-1α-ethyl-1β-/2',2'-diethoxycarbonylethyl/-1,2,3,4,6,7,12bα-octahydroindolo[2,3-a]quinolizine hydrochloride prepared according to the Belgian patent specification No. 883,576 the base is liberated in 25 ml. of dichloromethane with 10 ml. of a 10% aqueous sodium carbonate solution. After separation the extraction is repeated by 5 ml. of dichloromethane. The organic phases are collected, dried over solid, anhydrous magnesium sulfate, filtered and from the filtrate the solvent is eliminated by distillation in vacuo.

The oily residue is dissolved in 15 ml. of absolute benzene, to the solution 258 mg. /2.3 mmoles/ of potassium tert.-butylate are added and the reaction mixture is refluxed under nitrogen atmosphere for 20 minutes.

After cooling, under cooling with ice the reaction mixture is neutralized to pH 6 with acetic acid and the solvent is then eliminated by distillation in vacuo. The evaporation residue is dissolved in 20 ml. of dichloromethane, the solution is shaken with 10 ml. of a 5% aqueous sodium carbonate solution to adjust the pH to 9. After separation the extraction is repeated with a further 5-ml. portion of dichloromethane and the organic phase is separated. The combined organic phases are dried over solid, anhydrous magnesium sulfate, filtered and from the filtrate the solvent is eliminated by distillation in vacuo.

960 mg. of an oily product are obtained, which is then crystallized from 1.5 ml. of methanol.

480 mg. of the aimed compound are obtained.

Yield: 66.5%.

Melting point: 143° to 144° C. /ethanol/.

IR spectrum /KBr/: 1738 /ester/, 1690 cm$^{-1}$ /lactame/.

Mass spectrum /m/e, %/: 380 /M$^+$, 100/, 379/35/, 363/20/, 352/17/, 351/26/, 335/12/, 323/9.1/, 307/55/, 252/35/, 237/17/.

1H-NMR sepctrum /CDCl3, δ/: 8.52–7.35 /4H, m, aromatic/, 4.31 /2H, q, J=7, 2 Hz, OCH2/, 4.08 /1H, m, 3-H/, 3.75 /1H, d, J=11 Hz, 15-H/, 1.34 /3H, t, J+7.6 Hz, OCH2CH3/, 0.91 /3H, t, J+8.1 Hz, CH2CH3/.

EXAMPLE 2

/±/-Trans-14-oxo-15-ethoxycarbonyl-E-homo-eburnane/3α,17α/

400 mg. /0.94 mmoles/ of /±/-1α-ethyl-1β-/2',2'-diethoxycarbonyl-ethyl/-1,2,3,4,6,7,12,12b β-octahydroindolo[2,3-a]quinolizine obtained as a by-product in Example 1 of the Belgian patent specification No. 883,576 are dissolved in 10 ml. of absolute benzene, then 125 mg. /1.11 mmoles/ of potassium tert.-butylate are added to the solution. The reaction mixture is refluxed under nitrogen atmosphere for 20 minutes.

The pH of the reaction mixture is adjusted to 6 with acetic acid under cooling with ice. The solvent is evaporated in vacuo, the residue is dissolved in 10 ml. of dichloromethane and the solution is shaken with a 5% aqueous sodium carbonate solution to adjust the pH to 9. The extraction is repeated with a further 5-ml. portion of dichloromethane, and the combined organic phases are dried over solid anhydrous magnesium sulfate, filtered and from the filtrate the solvent is eliminated by distillation in vacuo. 300 mg. of an oily product are obtained which is then crystallized from 2 ml. of ethanol.

260 mg. of the aimed compound are obtained.
Yield: 73.0%.
Melting point: 173° to 175° C./ethanol/.
IR spectrum /KBr/: 2750–2700 /Bohlmann/, 1735 /ester/, 1680 cm$^{-1}$ /lactame/.
Mass spectrum /m/e, %/: 380 /M$^+$, 100/, 379/38/, 363/14/, 352/11/, 351/16/, 335/11/, 323/5.5/, 307/34/ ...
1H-NMR spectrum /CDCl3, δ/: 8.56–7.24 /4H, m, aromatic protones/, 4.32 /2H, q, J=7.6 Hz, OCH2/, 4.08 /1H, dd, J1=13.6 Hz J2=2.7 Hz, 15-H/, 3.41 /1H, s, 3-H/, 1.35 /3H, t, J=7, 6 Hz, OCH2CH3/, 0.74 /3H, t, J=6 Hz, CH2CH3/.

EXAMPLE 3

/±/-Cis-14-oxo-15-ethoxycarbonyl-E-homo-eburnane/3α,17α/

From 634.5 mg. and 698.0 mg. /1 mmole/ of /±/-1α-ethyl-1β-/2',2',4',4'-tetraethoxycarbonylbutyl/-1,2,3,4,6,7,12,12bα-octahydroindolo[2,3-a]quinolizine hydrochloride and hydrogen perchlorate, respectively, the corresponding base is liberated with 10 ml. of a 10% aqueous sodium carbonate solution in 25 ml. of dichloromethane. The organic phases are combined, dried over solid, anhydrous magnesium sulfate, filtered and from the filtrate the solvent is distilled off in vacuo.

The residual oil is dissolved in 15 ml. of absolute benzene, then 145 mg. /1.3 mmoles/ of potassium tert.-butylate are added to the solution and the reaction mixture is refluxed under nitrogen atmosphere for half an hour. The reaction mixture is cooled down and its pH is adjusted to 6 with acetic acid. The solvent is distilled off in vacuo, the residue is dissolved in 10 ml. of dichloromethane, the solution is alkalized with 10 ml. of a 5% aqueous sodium carbonate solution to pH 9 and is then extracted with a further 5-ml. portion of aqueous dichloromethane. The organic phases are collected, dried over solid, anhydrous magnesium sulfate, filtered and from the filtrate the organic solvent is eliminated by distillation in vacuo. The residual oily product is crystallized from 1 ml. of ethanol.

307 mg. of the aimed compound are obtained.
Yield: 80.8%.
Melting point: 143° to 144° C./ethanol/

EXAMPLE 4

/±/-Cis-14-oxo-15-ethoxycarbonyl-E-homo-eburnane/3α,17α

The procedure described in Example 3 is followed starting from 870 mg. /1 mmole/ of /±/-1α-ethyl-1β-/2',2',4',4',6',6'-hexaethoxycarbonylhexyl-1,2,3,4,6,7,12,-12bα-octahydroindolo[2,3-a]quinolizine hydrogenperchlorate prepared according to the Belgian patent specification No. 883,576.

264 mg. of the aimed compound are obtained.
Yield: 69.5%.
Melting point: 142° to 143° C. /ethanol/.

EXAMPLE 5

/±/-Cis-14-oxo-15-ethoxycarbonyl-E-homo-eburnane/3α,17α/hydrochloride 200 mg. of /±/-cis-14-oxo-15-ethoxycarbonyl-E-homo-eburnane/3α,17α/ are dissolved in a mixture of 3 ml. of dichloroethane and 2 ml. of ethyl alcohol and the pH of the solution is adjusted to 2 with hydrochloric acid in ethanol. The reaction mixture is evaporated to dryness and the evaporation residue is crystallized from 1.5 ml. of ethanol.

165 mg. of the aimed compound are obtained.
Yield: 75.2%.
Melting point: 204° to 207° C. /toluene/.

EXAMPLE 6

/±/-Cis-14-oxo-15-ethoxycarbonyl-E-homo-eburnane/3α,17α

300 mg. of /±/-1α-ethyl-1β-/2'-carboxy-2'-ethoxycarbonylethyl/-1,2,3,4,6,7,12,12bα-octahydroindolo[2,3-a]quinolizine prepared according to Example 5 or Example 6 of the Belgian patent specification No. 883,576 are suspended in 2 ml. of absolute benzene and 2 ml. of phosphorus oxychloride are added to the suspension under cooling with ice. The reaction mixture is then refluxed for 8 to 9 hours, with stirring.

The reaction mixture is cooled and is evaporated to dryness in vacuo. The residue is triturated with 2 ml. of ice water, its pH is adjusted to 9 with a 10% aqueous sodium carbonate solution and the organic substance is extracted with three 2-ml. portions of dichloromethane. The combined organic phases are dried over solid, anhydrous magnesium sulfate, filtered and from the filtrate the solvent is eliminated by distillation in vacuo. 226 mg. of an oily product are obtained, which is then crystallized from 0.5 ml. of ethanol.

156 mg. of /+/-cis-14-oxo-15-ethoxycarbonyl-E-homo-eburnane/3α,17α/ are obtained.
Yield: 54.3%.
Melting point: 142° to 144° C. /ethanol/.
IR spectrum /KBr/: 1725 /ester CO/, 1680 /lactame CO/.

We claim:
1. A racemic or optically active E-homo-eburnane of the formula (I),

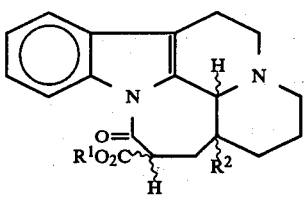 (I)

wherein
R[1] and R[2] independently represent an alkyl group having 1 to 6 carbon atoms,
and acid addition salts thereof.

2. A pharmaceutical composition for use as an anti-depressant or as an anti-hypoxial agent which comprises: as an active ingredient an effective amount of at least one racemic or optically active compound of the formula (I) as defined in claim 1 or a pharmaceutically acceptable acid addition salt thereof, in admixture with inert solid or liquid pharmaceutical carriers and/or additives.

3. A compound of the formula I of claim 1, which is a 3-beta, 17-alpha-trans compound.

4. A anti-hypoxial agent comprising: an effective amount of a compound as defined in claim 3 as an active agent or a pharmaceutically acceptable acid addition salt thereof, in admixture with inert solid or liquid pharmaceutical carriers and/or additives.

5. A compound of the formula I of claim 1, which is a 3-beta, 17-alpha-cis compound.

6. An anti-depressive agent comprising: an effective amount of a compound as defined in claim 5 as an active agent or a pharmaceutically acceptable acid addition salt thereof, in admixture with inert solid or liquid pharmaceutical carriers and/or additives.

* * * * *